United States Patent
Tokhtuev et al.

(10) Patent No.: US 6,842,243 B2
(45) Date of Patent: Jan. 11, 2005

(54) TURBIDITY SENSOR

(75) Inventors: Eugene Tokhtuev, Duluth, MN (US);
Christopher Owen, Duluth, MN (US);
Anatoly Skirda, Duluth, MN (US);
Viktor Slobodyan, Duluth, MN (US);
José Goin, Duluth, MN (US)

(73) Assignee: Apprise Technologies, Inc., Duluth, MN (US)

( * ) Notice: Subject to any disclaimer, the term of this patent is extended or adjusted under 35 U.S.C. 154(b) by 72 days.

(21) Appl. No.: 10/315,142

(22) Filed: Dec. 10, 2002

(65) Prior Publication Data

US 2003/0117623 A1 Jun. 26, 2003

Related U.S. Application Data

(60) Provisional application No. 60/337,165, filed on Dec. 10, 2001.

(51) Int. Cl.[7] .............................................. G01N 21/00
(52) U.S. Cl. ..................................................... 356/338
(58) Field of Search ................................ 356/335–343; 250/336, 341, 343, 344, 357, 338

(56) References Cited

U.S. PATENT DOCUMENTS

| | | | | |
|---|---|---|---|---|
| 3,888,269 A | * | 6/1975 | Bashark | ..................... 134/57 D |
| 4,197,458 A | * | 4/1980 | Perren | ..................... 250/341.2 |
| 4,707,134 A | * | 11/1987 | McLachlan et al. | ......... 356/342 |
| 4,841,157 A | * | 6/1989 | Downing, Jr. | .............. 250/574 |
| 4,962,395 A | * | 10/1990 | Baird | ......................... 340/619 |
| 5,233,860 A | * | 8/1993 | Mori et al. | .................. 73/19.1 |
| 6,324,900 B1 | * | 12/2001 | Bruno et al. | ................ 73/61.48 |
| 6,614,523 B1 | * | 9/2003 | Boss et al. | ................... 356/301 |
| 2003/0142316 A1 | * | 7/2003 | Schenkl et al. | ............. 356/442 |
| 2003/0214653 A1 | | 11/2003 | Palumbo et al. | |

OTHER PUBLICATIONS

International Search Report dated Jun. 30, 2004.

* cited by examiner

*Primary Examiner*—Michael P. Stafira
(74) *Attorney, Agent, or Firm*—Reed Smith LLP; Stanley P. Fisher, Esq.; Juan Carlos A. Marquez, Esq.

(57) ABSTRACT

A small size turbidity sensor for underwater in-situ measurements in the wide range of turbidity values is disclosed that may be integrated into a housing with other underwater sensors. The turbidity sensor incorporates micro focusing devices and light stop that gives no divergence excitation beam with convergence less than 1.5 degrees and the measuring angle between the optical axis of the incident radiation and mat of the diffused radiation 90 ±2.5 degrees. Another embodiment includes internal and external optical calibrators that allows the sensor to work longer without human intervention.

39 Claims, 8 Drawing Sheets

TURBIDITY SENSOR

This application claims the benefit of U.S. Provisional Patent Application Ser. No. 60/337,165 filed on Dec. 10, 2001, the entire disclosures of which are incorporated herein by reference.

BACKGROUND OF THE INVENTION

1. Field of the Invention

The invention relates generally to optical methods and apparatus for measuring turbidity of liquids and more particularly to methods and devices for the in-situ measurement turbidity of the natural water.

2. Description of Related Arts

Turbidity sensing provides a quick, practical indication of the relative amount of suspended solids in water or suspended liquids. Many industrial and commercial bath applications can make use of integrated turbidity and conductivity sensing to improve product quality, minimize ingredient consumption, and reduce wastewater discharge. However, the inventors focused on in-situ measurement turbidity of the natural water for environmental monitoring.

U.S. Pat. No. 5,589,935 describes turbidity sensor with the capability of regulating the intensity of a light source. This sensor operates by measuring transmission light but not scattering light such that it cannot measure low turbidities of natural water of rivers, lakes and reservoirs. The turbidity sensors disclosed by U.S. Pat. No. 5,828,458 and U.S. Pat. No. 5,596,408 operate with a LED (light emitting diode) and photodiodes thereby measuring turbidity using scattering and transmission. However, they require special test cells or covers, and they cannot measure turbidity in-situ.

There are two standard specifications for turbidity that are generally in use worldwide. These are the International Standard ISO 7027 (Water quality—Determination of Turbidity, International Standard, Third Edition, 1999-12-15) and the USEPA 180.1 (Nephelometric Method 2130 B, Standard Methods for the Examination of Water and Wastewater, 1989) Both methods measure the intensity of light scattered at 90.degree to the path of incident light. The specification of the ISO standard is more stringent and requires the use of a monochromatic light source. This specification allows for greater reproducibility of a measured values and greater agreement between other measuring instruments (http://www.omega.comltechref/ph-6.html).

The turbidity sensors described in U.S. Pat. No. 5,350,922 and U.S. Pat. No. 4,841,157 use LED light sources to operate with broad range of scattering angles rather than at 90°, and their optical designs are very different from the requirements of the standard ISO 7027. The turbidity sensor described in an article by Saba Mylvaganam titled "Turbidity Sensor For Underwater Applications" has an excitation beam with a big divergence and measures the light backscattered at the average angle 145° instead of 90° as it is recommended in the standard ISO 7027 (article is available at http://www.aanderaa.com/PDF Files/Articles_$T_D$_TN/Turbidity%20Sensor%20Design%20and%20performance.pdf)

Currently, there is no portable in-situ measurement turbidity sensor for the natural water which operation complies with the standard ISO 7027 and can be freely calibrated by the user with ease and convenience.

SUMMARY OF THE INVENTION

It is another object of the present invention to improve a turbidity sensor with a smaller size that may be integrated into a housing already comprising other sensors.

It is another object of the present invention to improve the performance of a turbidity sensor with a design measuring the scattered radiation at the wavelength 860 nm with bandwidth 60 nm as required by the International Standard ISO 7027 "Water Quality—Determination of Turbidity".

It is another object of the present invention to improve a turbidity sensor with a smaller size and may be integrated into a housing already comprising other sensors.

It is a further object of the present invention to provide a mechanism to periodically calibrate a turbidity sensor in the laboratory and in the field.

Other objects and advantages of the present invention may be seen from the following detailed description.

In accordance with the present invention, a turbidity sensor is built with micro focusing devices that allow for decreasing the size of the sensor body while achieving high sensitivity due to higher intensity of excitation light in the analytical area. The turbidity sensor with micro focusing devices has a smaller size and may be integrated into a housing already occupied by other sensors. The turbidity sensor according to the present invention uses lenses with diameter 3.9 mm. An optical assembly of the turbidity sensor has dimensions 20 mm ×15 mm×8 mm. The electronic board for this sensor has size 10 mm×50 mm. The turbidity sensor with micro focusing devices has better signal to noise ratio and may operate with the light emitting diode(s) and photodiode(s) placed directly near the micro focusing devices or alternatively with the light emitting diode(s) and photodiode(s) placed inside the housing using optic fibers of a small diameter to couple the light emitting diode(s) and photodiode(s) with the micro focusing devices. This turbidity sensor with micro focusing devices results in an optical design, which is closer to the requirements of the International Standard ISO 7027. Micro focusing devices, according to the present invention, include prismatic members to compensate difference in refractive indexes of water and glass or plastic parts used for light collimating.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein.

DETAILED DESCRIPTION OF THE INVENTION

Figure 1:
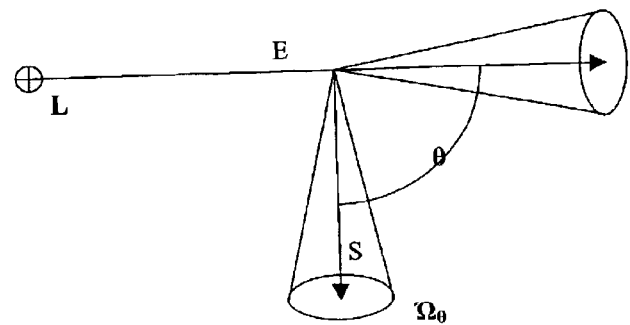
FIG. 1 illustrates the scattering and transmission parameters as defined in ISO 7027.

According the ISO 7027, the turbidity should be measured by measuring the scattered radiation at the wavelength 860 nm with bandwidth 60 nm. Referring to the FIG. 1, the optical configuration for the turbidity measurements by measuring diffused radiation (ISO 7027). In FIG. 1, L represents a light source to produce incident radiation with no divergence, E represents the direction of a excitation beam, S represents the direction of a scattered radiation, .theta. represents the measuring angle between the optical axis of the incident radiation and mat of the diffused radiation, and .OMEGA . . . sub.0 represents the aperture angle in the water sample. The light source L produces an infrared beam with no divergence and convergence should be not more than 1.5 degrees. The measuring angle .theta. between the optical axis of the incident radiation and the mat of the diffused radiation should be 90±2.5 degrees. The aperture angle .OMEGA . . . sub.0 in the water sample should be between 20 degrees and 30 degrees.

A turbidity sensor according to the present invention includes a watertight housing with optical windows, a light emitting diode connected to the pulse generator, first light focusing device forming a light beam, a second light focusing device collecting the scattered light, a photodiode sensing the scattered light, and an electronic board having a lock-in amplifier and signal processing capability.

Figure 2:
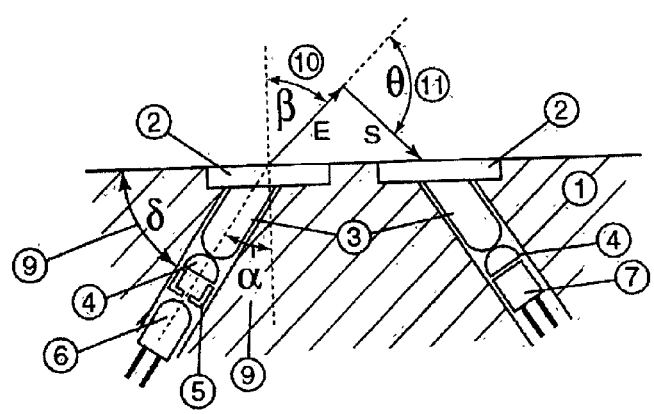
FIG. 2 shows the optical design of one embodiment of a turbidity sensor head with micro focusing devices according to the present invention.

An optical design of the turbidity sensor head is shown in the FIG. 2 which includes a watertight housing 1, two optical windows 2, a pair of prismatic focusing devices 3, two lens 4, a light stop 5, a light emitting diode 6, and a photodiode 7. The watertight housing 1 is made of plastic, such as PVC, or metal, such as stainless steel or aluminum, and has counterbored holes for windows and cylindrical channels. The optical windows 2 are preferably made from sapphire with a high scratch and wear resistance. The prismatic focusing devices 3 are made from cylinders of optical glass BK 7 or sapphire. Each of the cylinders a polished spherical end and a polished flat end. The cylinders are glued to the windows 2 and inserted into a pair of cylindrical channels tilted relatively to the counterbored holes for optical windows. The lens 4 is placed near the prismatic focusing devices 3 to improve beam collimating. The light stop 5 is placed in the first cylindrical channel in front of the light emitting diode 6. There is another lens 4 in front of a photodiode 7 in the second cylindrical channel. Both channels are tilted relatively to the window at the same angle .delta. (marked 8) from the flat upper surface of the housing. The angle between the normal to the window and the cylinder axis equals .alpha.(=90.degree.-.delta.; marked 9). The incidence angle .alpha. should be chosen in such way that the refraction angle .beta. (marked 10) between the normal to the window and the direction of beam in water should be 45.degree. The incidence angle a depends on the refractive index of the material used for the prismatic focusing device. The refraction angle .beta. equals 45.degree. if the incidence angle a corresponds to equation (1). 1 Sin ( )=Np Sin (45.degree. ) N w (1)

$$\operatorname{Sin}(\alpha) = \frac{N_p \cdot \operatorname{Sin}(45°)}{N_w} \quad (1)$$

Where $N_p$—refractive index of the material used for the prismatic focusing device $N_w$—refractive index of water Table 1 shows incidence angles for two materials of prismatic focusing devices. The refractive indexes in Table 1 are shown for the wavelength 850 nm.

TABLE 1

| Material of prismatic focusing device | $N_p$— refractive index of the material used for the prismatic focusing device | $N_w$— refractive index of water | Refraction angle β | Incidence angle α | Angle between flat surface and cylinder axis δ |
|---|---|---|---|---|---|
| Glass BK 7 | 1.501 | 1.329 | 45° | 38.8° | 51.2° |
| Sapphire | 1.759 | 1.329 | 45° | 32.3° | 57.7° |

For the turbidity sensor built according to FIG. 1 and with materials and angles according to the Table 1, the measuring angle θ (marked 11) equals 90°. Arrows E and S represent the direction of an excitation beam and the direction of the scattered radiation respectively.

Figure 3:
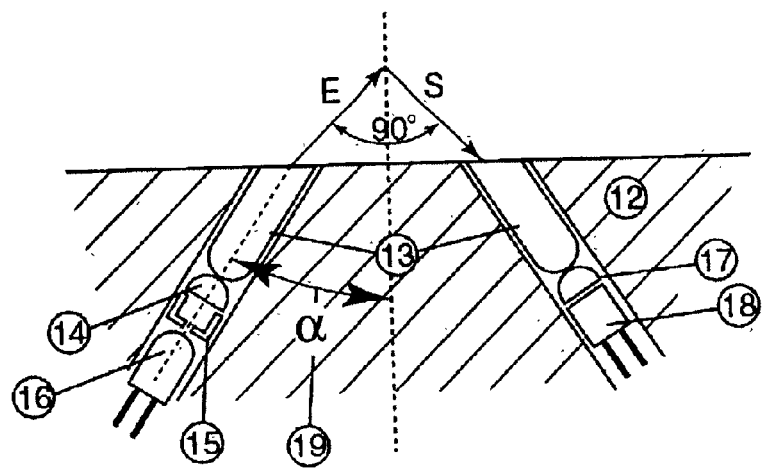
FIG. 3 shows the optical design of one embodiment of a turbidity sensor head with prismatic focusing devices that serve as windows, light stops and other two focusing lenses according to the present invention.

The optical design of the turbidity sensor head with prismatic lenses without additional windows is shown in the FIG. 3. The turbidity sensor head has a watertight housing 12 with cylindrical channels, two optical windows 2, a pair of prismatic focusing devices 13, lens 14 and 17, a light stop 15, a light emitting diode 16, and a photodiode 18. The prismatic lenses 13 are glued in the channels. The positive lens 14 is placed near the prismatic lens 13 to improve beam collimating. The light stop 15 is placed in the first cylindrical channel in front of the light emitting diode 16. The lens 17 is placed in front of the photodiode 18 in the second cylindrical channel. Both cylindrical channels are tilted relatively to the flat surface of the watertight housing 12. An angle α (marked 19) between the cylinder axis and the flat upper surface of the turbidity sensor head is chosen to provide a refraction angle of 45° after the beam refraction in water and an angle of 90 between the direction of excitation beam E and direction of the scattered radiation S.

Figure 4:
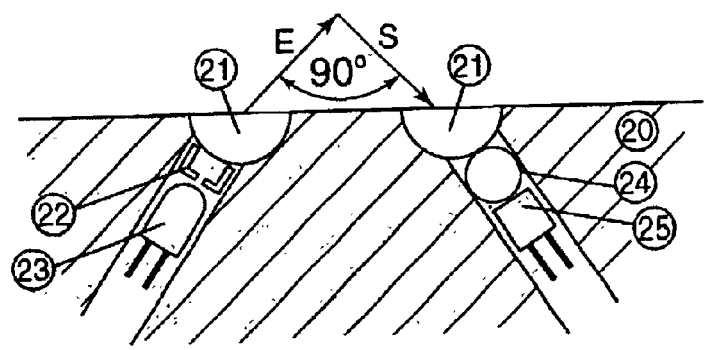
FIG. 4 shows the optical design of one embodiment of a turbidity sensor head with half ball lenses according to the present invention.

The optical design of the turbidity sensor head with half ball lenses is shown in the FIG. 4. A turbidity sensor head has a watertight housing 20 with half spherical cavities and cylindrical channels. Half ball lenses 21 are glued into the half spherical cavities. A light stop 22 and a light emitting diode 23 are placed inside of one cylindrical channel. A ball lens 24 and a photodiode 25 are placed inside of the other cylindrical channel. The cylindrical channels are tilted relatively to the flat upper surface of the turbidity sensor head to provide a refraction angle of 45° after the beam refraction in water and an angle of 90 between the direction of excitation beam E and direction of the scattered radiation S.

Figure 5:
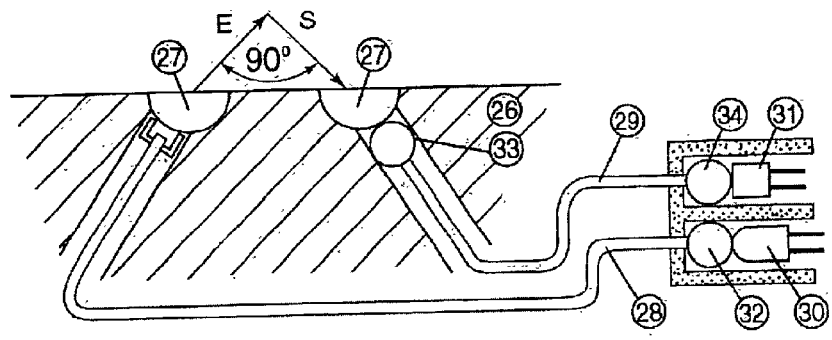
FIG. 5 shows the optical design of one embodiment of the turbidity sensor head with half ball lenses and optic fibers according to the present invention.

The optical design of the turbidity sensor head with half ball lenses and optic fibers is shown in the FIG. 5. A turbidity sensor head has a watertight housing 26 with half spherical cavities and cylindrical channels. Half ball lenses 27 are glued into the half spherical cavities. Optic fibers 28 and 29 are inserted into the cylindrical channels to transmit the excitation light from a light emitting diode 30 and to bring a scattered light to a photodiode 31. A ball lens 32 is placed between the light emitting diode 30 and the optic fiber 28. A ball lens 33 directs the scattered light into the optic fiber 29 and then a ball lens 34 directs the scattered light from the optic fibers 29 to a photodiode 25. The cylindrical channels are tilted relatively to the flat upper surface of the turbidity sensor head to provide a refraction angle of 45° after the beam refraction in water and an angle of 90 between the direction of excitation beam E and direction of the scattered radiation S.

Figure 6:
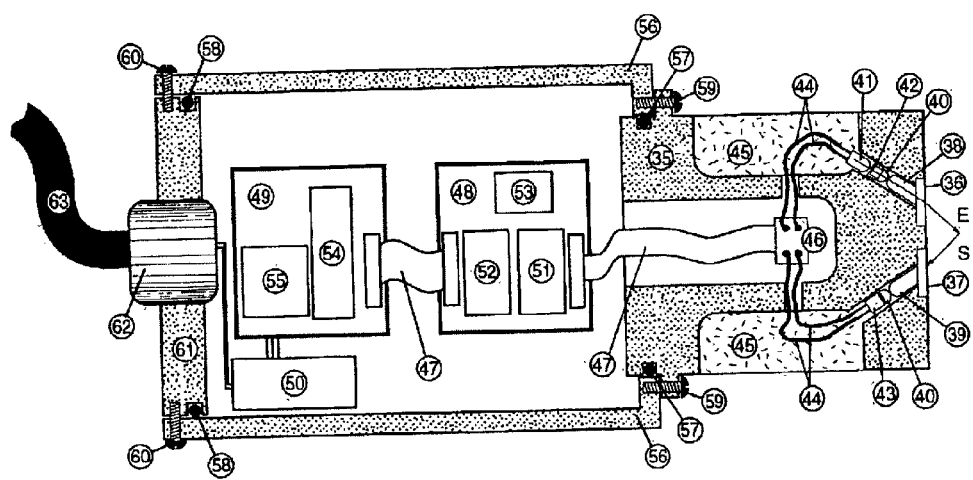
FIG. 6 shows a turbidity sensor for underwater measurements according to the present invention.

One embodiment of a turbidity sensor for underwater measurements according to the invention is shown in the FIG. 6. It comprises a sensor head 35 with tilted channels. The sensor head 35 has optical windows 36 and 37 made of sapphire. Focusing devices 38 and 39 are prismatic lenses made cylindrical and of optical glass BK 7 or sapphire. Each of the cylinders has a polished spherical end and a tilted, polished flat end. The prismatic lenses 38 and 39 are glued to the windows 36 and 37 and inserted into the cylindrical channels tilted relatively to the optical windows. A positive lens 40 is placed near the prismatic lens 38. A light emitting diode 41 is separated by a light stop 42 from the prismatic lens 38 to form an excitation beam E having no divergence in a small sample volume in front of the sensor head. A scattered radiation (of the angle 90°) is focused onto the photodiode 43. There is another positive lens 40 between the prismatic lens 39 and the photodiode 43 to increase optical efficiency. A pair of wires 44 are soldered to a connector 46 and the light emitting diode 40 as well as to the connector 46 and the photodiode 41. They are inserted inside of the sensor head and sealed with a potting compound 45. For example, Resinlab EP1056LC Black carried by Ellsworth Adhesives in Germantown, Wis. may be used as the potting compound. A flat cable 47 connects the connector 46 to a sensor board 48 so as to connect the light emitting diode 41 and the photodiode 43 to the sensor board 48. A second flat cable connects the sensor board 48 to a controller board 49. A power supply 50 receives power from a battery outside of the sensor to provide all voltages needed for the operation of the sensor and the controller boards. The sensor board 48 includes a preamplifier 51, a lock-in amplifier 52, and a pulse generator 53. The controller board 49 includes an ADC converter 54 and a communication means 55. The communication means 55 are an RS-232 to connect the turbidity sensor to a computer. Electronic boards are placed into a watertight housing 56. O-Rings 57 and 58 protect an interior volume of the turbidity sensor against the outside water pressure at the depth up to 200 meters. Screws 59 and 60 secure the sensor head 35 and a connector holder 61 at the watertight housing 56. A connector 62 connects the turbidity sensor to an underwater cable 63. For some embodiments the sensor board 48 is installed inside of the sensor head 35.

Figure 7A:
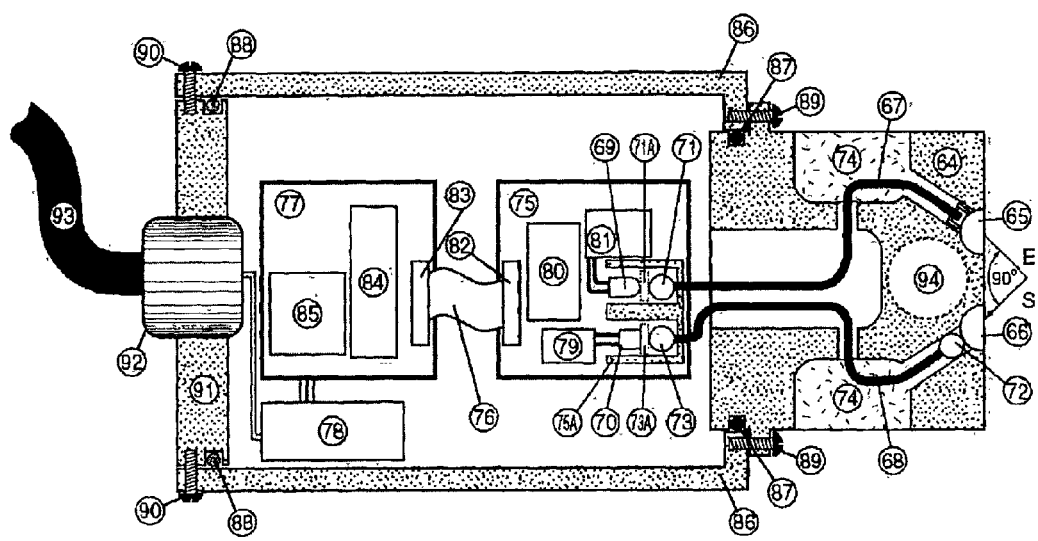
FIG. 7A shows a turbidity sensor with focusing devices and optic fibers according to the present invention.
Figure 7B:
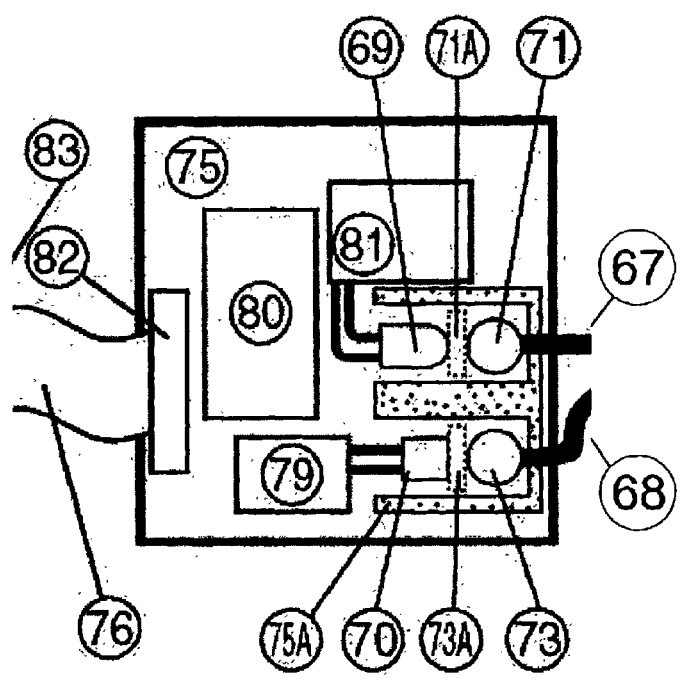
FIG. 7B shows an embodiment of the sensor board with an optical mount having optical filters inside according to the present invention.

Another embodiment of turbidity sensor with focusing devices and optic fibers is shown in the FIG. 7A. It comprises a sensor head 64 with tilted channels. The sensor head 64 has half spherical cavities and cylindrical channels. Half ball lenses 65 and 66 are glued into the half spherical cavities. Optic fibers 67 and 68 are inserted into the cylindrical channels to transmit an excitation light from a light emitting diode 69 and to bring the scattered light to a photodiode 70. The ball lens 71 is placed between the light emitting diode 69 and the optic fibers 67. The ball lens 72 directs the scattered light into the optic fibers 68, and then the ball lens 73 directs the scattered light from the optic fibers 68 to the photodiode 70. The cylindrical channels are tilted relatively to the flat upper surface of the sensor head 64 to provide a refraction angle of 45° after the beam refraction in water, and an angle of 90 between the direction of excitation beam E and direction of the scattered radiation S. The optic fibers 67 and 68 are inserted inside of the sensor head 64 and sealed with a potting compound 74. The light emitting diode 69, the photodiode 70, the ball lens 71, and the ball lens 73 are placed inside of an optical mount 75A made of an opaque material, such as aluminum or black PVC, to ensure that the photodiode 70 receives only the light from the optical fiber 68. A flat cable 76 connects the sensor board 75 to a controller board 77. A power supply 78 receives power from a battery outside of sensor to provide all voltages needed for the operation of the sensor and the controller boards. The sensor board 75 includes a preamplifier 79, a lock-in amplifier 80, a pulse generator 81, and a connector 82. The controller board 77 includes a connector 83, an ADC converter 84 and a communication means 85. The communication means 85 includes a RS-232 unit to connect the turbidity sensor to a computer. Electronic boards are placed into a watertight housing 86. O-Rings 87 and 88 protect an interior volume of the turbidity sensor against the outside water pressure at the depth up to 200 meters. Screws 89 and 90 secure the sensor head 64 and a connector holder 91 at the watertight housing 86. A connector 92 connects the turbidity sensor to an underwater cable 93. Some embodiments may include additional sensors, such as a depth sensor and/or fluorescent sensor, installed inside of the sensor head 64 in the reserved area 94. In another embodiment of the sensor board 75, optical filters 71A and 73A are placed between the light emitting diode 69 and the ball lens 71 as well as between the photodiode 70 and the ball lens 73. The enlarged view of the sensor board 75 is shown at the FIG. 7B. The optical filters 71A and 73A may have identical transmission bands for measuring turbidity. For example, both filters are narrow band infrared filters with the maximum transmission at 860 nm, and economical parts are used such as a cheap infrared light emitting diode with a broadband emission (e.x. LN68-ND carried by Digi-Key in Thief Rever Fall, Minn.) and a cheap silicon photodiode with a broad spectral range (e.x. PN323BPA-ND also carried by Digi-Key in Thief Rever Fall, Minn.). Alternatively, the optical filters 71A and 73A are interference filters with different transmission bands for measuring photosyntetyc pigments. For example, the optical mount 75A in such an alternative embodiment includes (i) the light emitting diode 69 made of GaN, (ii) the optical filter 71A with the maximum transmission in blue range of spectrum, (iii) the photodiode 70 made of silicon, and (iv) the optical filter 73A with the maximum transmission in red range of spectrum The optical mount 75A so composed produces an electrical signal proportional to the concentration of fluorescent materials, such as photosynthetic pigments or rodamine. The positions and bandwidths of such optical filters should be optimized to provide better selectivity for each specific application. For an even better selectivity to measure Chlorophyll A, the optical mount 75A includes (i) the light emitting diode 69 made of GaN, (ii) the optical filter 71A with a maximum transmission range of 420 nm to 440 nm, (iii) the photodiode 70 made of silicon, and (iv) the optical filter 73A with a maximum transmission range of 660 nm to 690 nm. To further improve selectivity, one or both filters are made with one or several parts having maximum transmissions at different wavelengths therein such that the filters are movable to change both the wavelength of radiation directed into the fiber 67 and the wavelength of radiation measured by the photodiode 70.

Figure 8A:
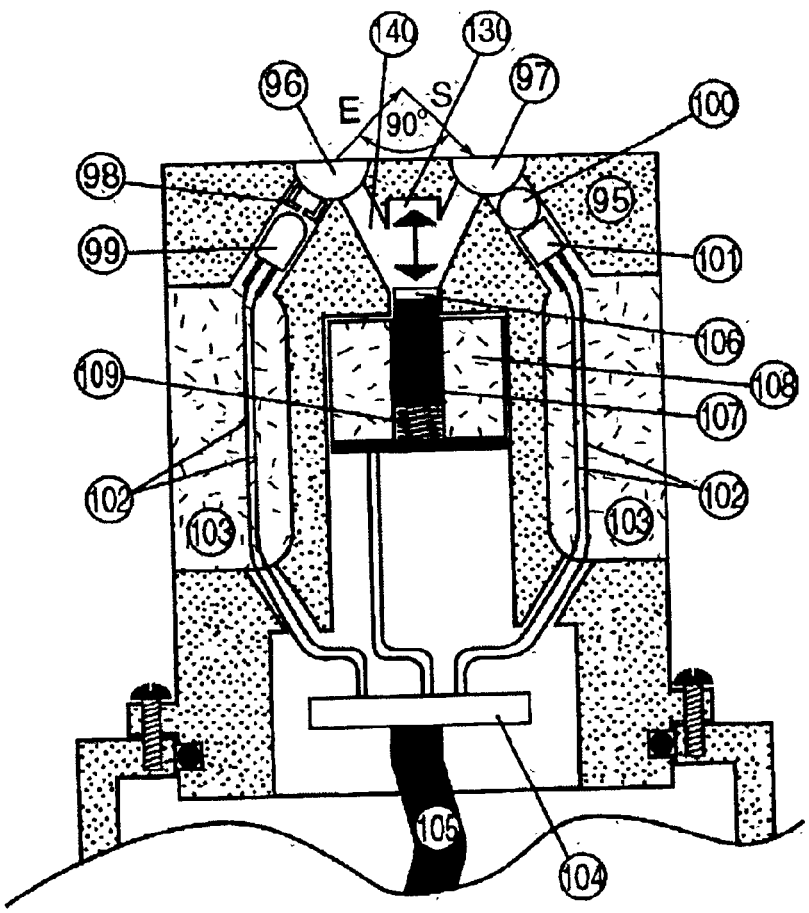
FIG. 8A shows a turbidity sensor with an internal optical calibrator according to the present invention.
Figure 8B:
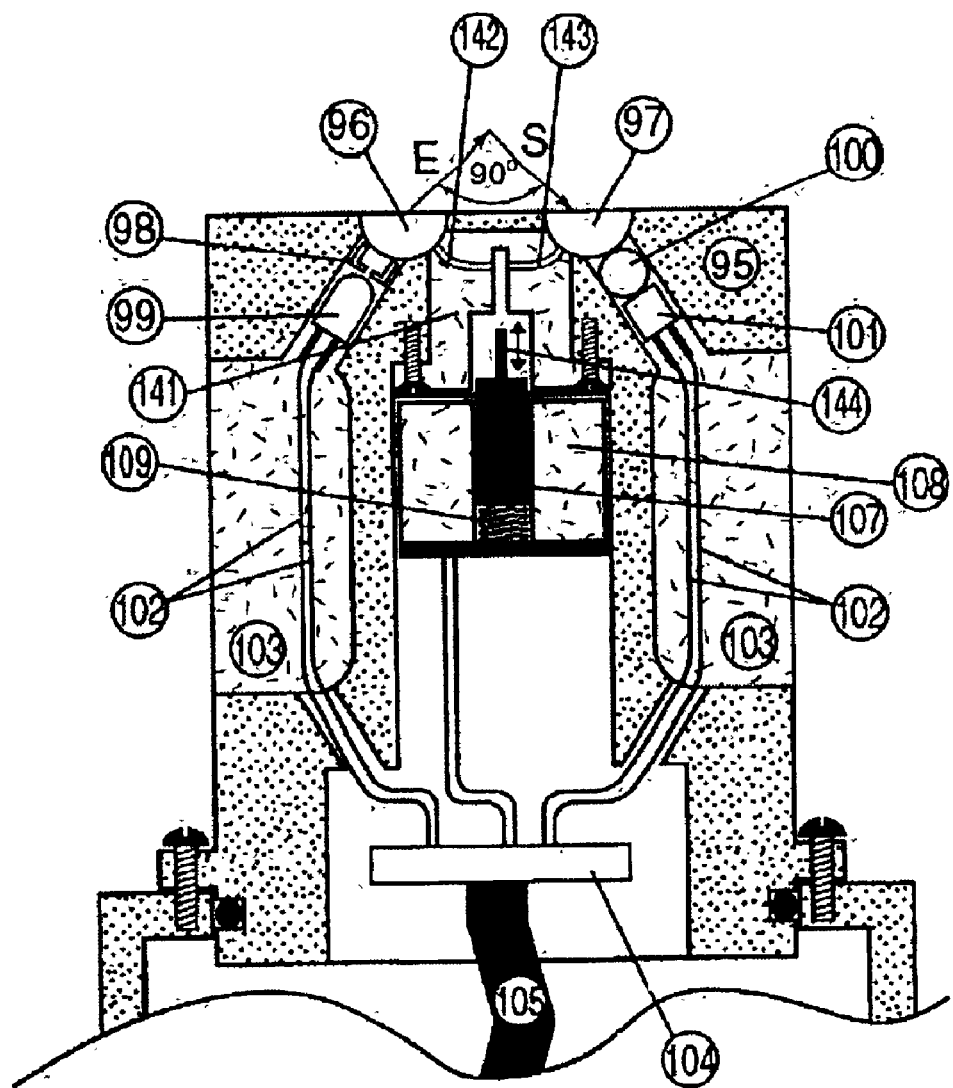
FIG. 8B shows a turbidity sensor with an internal optical calibrator made with two optical fibers according to the present invention.

A turbidity sensor with an internal optical calibrator is shown in the FIG. 8A. The internal optical calibrator is provided for periodically testing the sensitivity of the turbidity sensor. The internal calibrator allows the sensor work longer without human intervention by compensating any degradation of the light emission diode and the photodiode. For these purposes, the turbidity sensor has means (such as mirrors, windows, lenses, fiber optics, etc.) to direct periodically the part of excitation beam to the photodiode to receive a reference signal. The current reference signal is compared with the standard reference signal received during calibration, and current turbidity readings are corrected by multiplying to the ratio of standard and current reference signals. The turbidity sensor comprises a sensor head 95 with tilted channels. The sensor head 95 has two half spherical cavities and two cylindrical channels. Half ball lenses 96 and 97 are glued into the half spherical cavities. A light stop 98 and a light emitting diode 99 are placed inside of one cylindrical channel. A ball lens 100 and a photodiode 101 are placed inside the other cylindrical channel. The cylindrical channels are tilted relatively to the flat upper surface of the turbidity sensor head to provide a refraction angle of 45.degree. after the beam refraction in water, and an angle of 90.degree. between the direction of excitation beam E and direction of the scattered radiation S. A/pair of wires 102 are soldered to a connector 104 and the light emitting diode 99 as well as to the connector 104 and the photodiode 101. They are inserted inside of the sensor head and sealed with a potting compound 103. A flat cable 105 connects the light emitting diode 99 and the photodiode 101 to a sensor board inside the watertight housing of the turbidity sensor. The internal optical calibrator comprises a mirror 106 fixed at a moving piston 107 and an electromagnet 108. The mirror is situated in two positions. In the first position, when there is no current through the electromagnet 108, a spring 109 moves the mirror 106 and the piston 107 out of the electromagnet 108 into the cavity 130. In the second position, when there is a current through the electromagnet 108, the mirror 106 and the piston 107 are pulled inside the electromagnet 108. There are two additional channels 140 inside of the sensor head 95. When the mirror 106 is in the first position,the piston 107 blocks a part of an excitation light reflected from the surface of first half ball lens. When the mirror 106 is in the second position, the mirror 106 directs a part of the excitation light reflected from the flat surface of first half ball lens into the second additional channel. As such, the part of this light reflected from the flat surface of second half ball lens reaches the photodiode 100 and gives a reference signal. Another embodiment of the turbidity sensor with an internal optical calibrator is shown at the FIG. 8B. The turbidity sensor comprises a sensor head 95 with tilted channels. The sensor head 95 has two half spherical cavities and two cylindrical channels. Half ball lenses 96, 97 are glued into the half spherical cavities. A light stop 98 and a light emitting diode 99 are placed inside of one cylindrical channel. A ball lens 100 and a photodiode 101 are placed inside the other cylindrical channel. The cylindrical channels are tilted relatively to the flat upper surface of the turbidity sensor head 75 to provide a refraction angle of 45.degree. after the beam refraction in water, and an angle of 90.degree. between the direction of excitation beam E and the direction of the scattered radiation S. A pair of wires 102 are soldered to a connector 104 and the light emitting diode 99 as well as to the connector 104 and the photodiode 101. They are inserted inside of the sensor head 95 and sealed with a potting compound 103. A flat cable 105 connects the light emitting diode 99 and the photodiode 101 to a sensor board inside the watertight housing of the turbidity sensor. The internal optical calibrator comprises an insert 141 having two pieces of optic fiber 142 and 143 and a channel for a moving piston 107. The moving piston 107 has an opaque shutter 144 fixed at one side of the moving piston 107 which can stop at two positions. In the first position, when there is no current flowing through the electromagnet 108, a spring 109 moves the piston 107 and the shutter 144 out of the electromagnet 108. In the second position, when there is a current flowing through the electromagnet 108, the piston 107 and the shutter 144 are pulled inside the electromagnet 108. When the shutter 144 is in the first position, a part of an excitation light reflected from the surface of the first half ball lens 96 into the optic fiber 142 is blocked by the shutter 144. When the shutter 144 is in the second position, the part of the excitation light is delivered from the optic fiber 142 into the optic fiber 143. Thereafter, the part of this light reflected from the flat surface of the second half ball lens 97, reaches the photodiode 100, and gives a reference signal.

Figure 9:
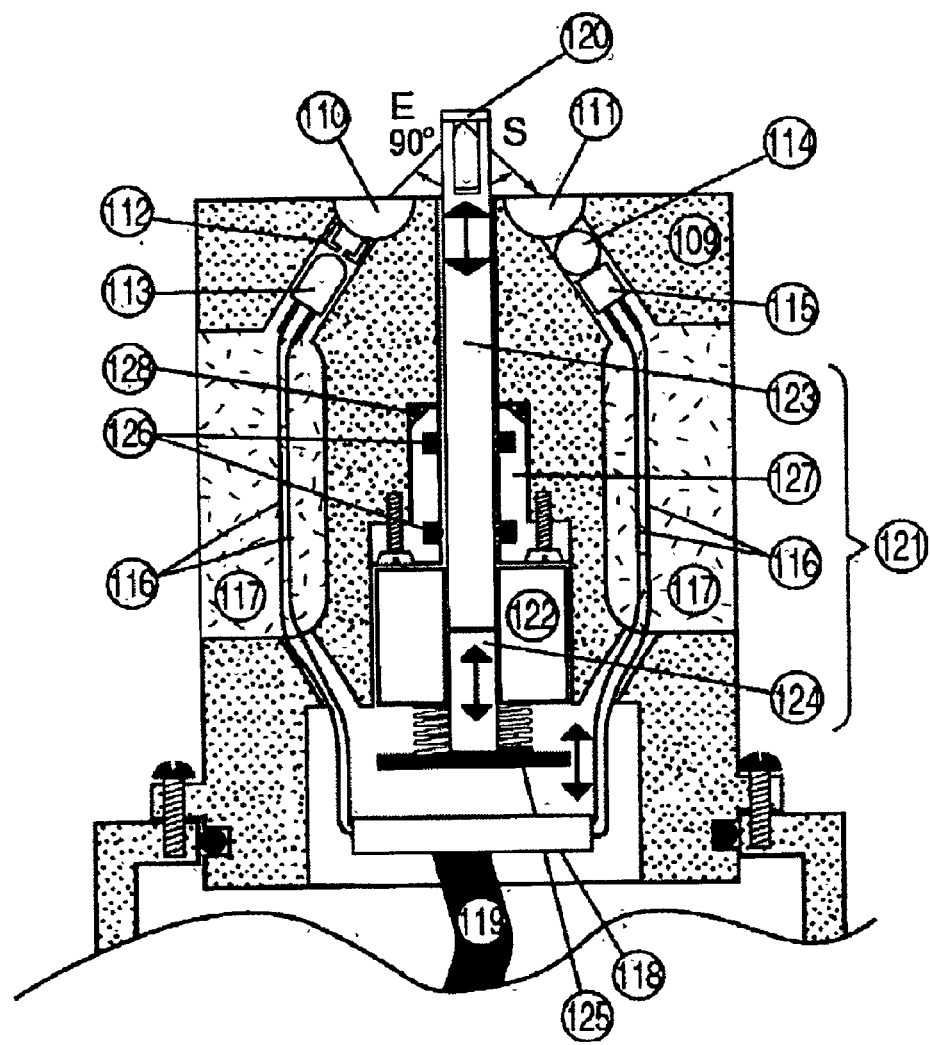
FIG. 9 shows a turbidity sensor with an external optical calibrator according to the present invention.

A turbidity sensor with an external optical calibrator is shown in the FIG. 9. The external optical calibrator for periodically testing the turbidity sensor allows the sensor to work longer without human intervention. The external optical calibrator directs periodically the part of an excitation beam from a first focusing device into a second focusing device so as to receive a standard reference signal from the photodiode. A current reference signal is compared with the standard reference signal received during calibration, and current turbidity readings are being corrected by multiplying to the ratio of standard and current reference signals. In this embodiment, the reference signal shows current changes in the optical part of the turbidity sensor. It provides not only a compensation of degradation of a light source and a photodiode therein, but also allows to compensate up to certain level of possible contaminations of the transparent surfaces of the turbidity sensor. The turbidity sensor with an external optical calibrator comprises a sensor head 109 with tilted channels. The sensor head 109 has two half spherical cavities and two cylindrical channels. Half ball lenses 110 and 111 are glued into the half spherical cavities. A light stop 112 and a light emitting diode 113 are placed inside one cylindrical channel. A ball lens 114 and a photodiode 115 are placed inside the other cylindrical channel. The cylindrical channels are tilted relatively to the flat upper surface of the turbidity sensor head to provide a refraction angle of 45.degree. after the beam refraction in water, and an angle of 90.degree. between the direction of excitation beam E and direction of the scattered radiation S. Pair of wires 116 are soldered to a connector 118 and the light emitting diode 113 as well as to the connector 118 and the photodiode 115. They are inserted inside of the sensor head and sealed with a potting compound 117. A flat cable 119 from the connector 118 connects the light emitting diode 113 and the photodiode 114 to a sensor board inside the watertight housing of the turbidity sensor. The external optical calibrator comprises a mirror 120 fixed at a movable piston 121, and an electromagnet 122. The movable piston 121 has a non-magnetic part 123 and a magnetic part 124. The piston is situated at two positions. In the first position, when there is no current through the electromagnet 122, a spring 125 pulls inwards the piston 121 such that the mirror 120 and the piston 121 are hidden inside of the sensor head 110. In the second position, when there is a current through the electromagnet 122, the mirror 120 and the piston 121 are pushed out by the magnet 122. In this position, the mirror 120 reflects a part of an excitation light into the second focusing device where it reaches the photodiode 115 and gives a reference signal. The movable piston 121 is sealed with an O-Rings 126 in a sealing insert 127 which is sealed by an O-Ring 128. The mirror 120 and the piston 121 most of the time are hidden inside of the sensor head 110 such that the mirror 121 is protected from possible contaminations and the reflection coefficient of the mirror 121 is kept more stable. To protect the mirror 121 from potential biofouling, the non-magnetic part 123 is made of copper or copper-nickel alloy, which has good antifouling properties and good corrosion resistance. The presence of copper ions in water near and around the mirror 121 inhibits the bio fouling and extends period of unattended work for the turbidity sensor.

Figure 10:
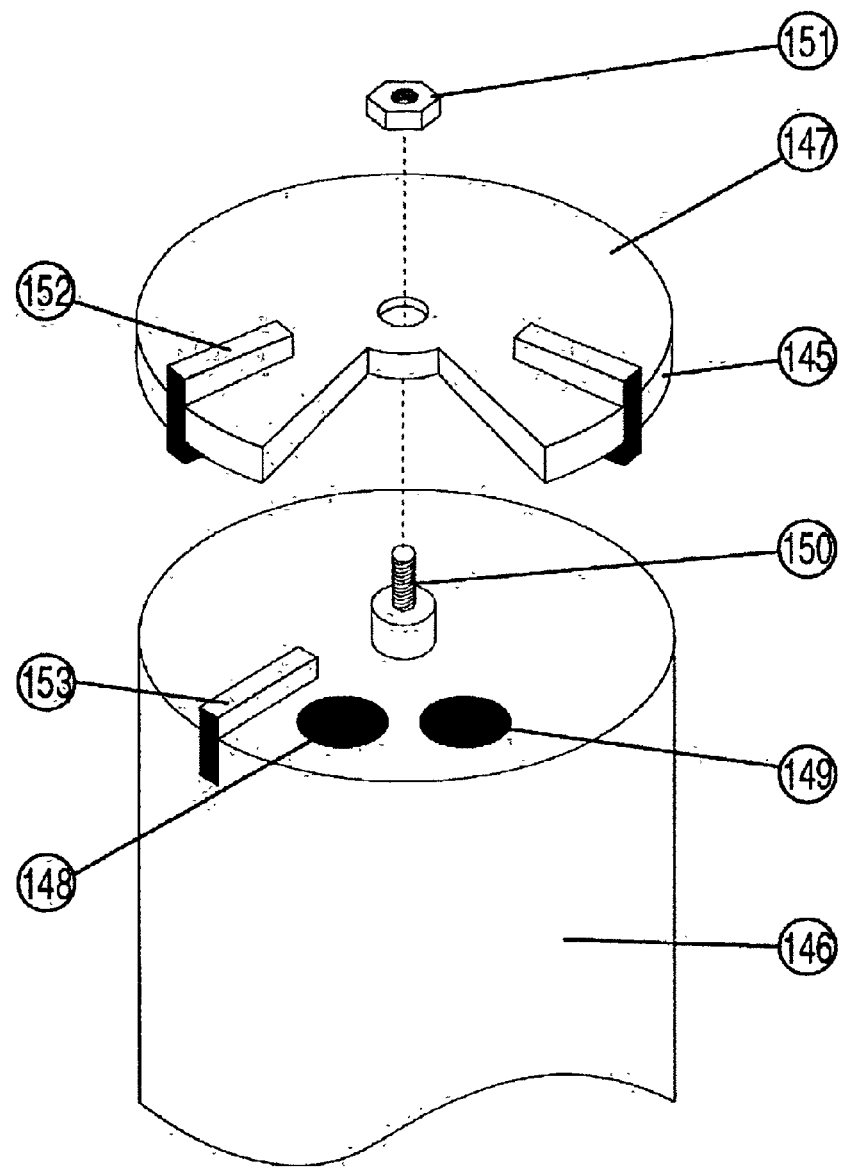
FIG. 10 shows another embodiment of a turbidity sensor with an external optical calibrator according to the present invention.

In another embodiment shown in FIG. 10, the optical calibrator is permanently placed outside of the watertight housing and made as a transparent member movable above the optical windows. A transparent member 145 has a hole that size is bigger than a window area at the sensor housing 146, and has one side transparent and another side comprising a reflective or diffusing surface 147 for directing a part of the excitation beam from the first window 148 into the second window 149. The transparent member 145 is fixed with a nut 150 at the shaft 151 of the geared electrical motor, which is placed inside of the sensor housing 146. The transparent member 145 has one or several soft cleaning members 152 to clean windows during rotation. Another soft cleaning member 153 is made like a ring and inserted into the grove near or around the windows. The cleaning member 153 cleans the surface of the transparent member 145 during rotation. During the normal operation, the transparent member 145 is positioned to allow turbidity measurements when the hole is above the windows. For calibration, the transparent member 145 is rotated for 180.degree. when both windows are under the transparent side of the transparent member 151. The excitation beam from the first window enters inside of the transparent member. After being reflected at the surface 147, it reaches the second window. The light from the calibrator is measured with a photodiode so as to provide a reference signal to correct turbidity readings during operation.

The principles, preferred embodiments and modes of operation of the present invention have been described in the foregoing specification. However, the invention that is intended to be protected is not limited to the particular embodiments disclosed. The embodiments described herein are illustrative rather than restrictive. Others may make variations and changes, and equivalents employed, without departing from the spirit of the present invention. Accordingly, it is expressly intended that all such variations, changes and equivalents that fall within the spirit and scope of the present invention as defined in the claims, be embraced thereby.

What is claimed is:

1. A turbidity sensor for underwater measurements, comprising:
    a watertight housing;
    a light emitting diode;
    a first light focusing device for focusing a light emitted from the diode and passing the focused light into to-be-measured water;
    a second light focusing device for collecting at least one scattered light resulted form the focused light when passing the water;
    a photodiode for receiving the collected light thereby generating electronic signals; and
    an electronic board for processing the electronic signals, wherein said watertight housing has cavities for accommodating the first and second focusing devices therein respectively, said cavities are shaved cylindrically and tilted with a first angle relatively to an upper surface of said watertight housing which is placed below a water surface, the first and second focusing devices are transparent cylinders having a flat end tilting relatively to a cylinder axis with a second angle so as to be in parallel with the upper surface of the housing and another end facing away from the upper surface, and the first angle is equal to the second angle, and said another end is a spherical surface for focusing light beam.

2. The turbidity sensor according to claim 1, further comprising two optical windows located in the watertight housing and in parallel with the upper surface of the watertight housing, and the windows are optically communicating with the flat tilted ends of said cylinders respectively.

3. The turbidity sensor according to claim 2, wherein said optical windows are made of sapphire.

4. The turbidity sensor according to claim 1, wherein said cylinders are made of glass, the second angle ranges from 49° to 53°, and the spherical end has a radius of 3 to 7 mm.

5. The turbidity sensor according to claim 1, wherein said cylinders are made of sapphire, the second angle ranges from 56° to 60°, and the spherical end has a radius of 4 to 8 mm.

6. A turbidity sensor for underwater measurements, comprising:
    a watertight housing;
    a light emitting diode;
    a first light focusing device for focusing a light emitted from the diode and passing the focused light into to-be-measured water;
    a second light focusing device for collecting at least one scattered light resulted form the focused light when passing the water;
    a photodiode for receiving the collected light thereby generating electronic signals; and
    an electronic board for processing the electronic signals, wherein said watertight housing has cavities for accommodating the first and second focusing devices therein respectively, said cavities are shared cylindrically and tilted with a first angle relatively to an upper surface of said watertight housing which is placed below a water surface, the first and second focusing devices are transparent cylinders having a flat end tilting relatively to a cylinder axis with a second angle so as to be in parallel with the upper surface of the housing and another end facing away from the upper surface, and the first angle is equal to the second angle, and further comprising a light stop placed inside one of the cavities and between the light emitting diode and said another end of a first cylinder of said cylinders such that a gap is provided between the light stop and said another end of the first cylinder.

7. The turbidity sensor according to claim 6, wherein said light stop has an opening with a diameter of 0.3 to 3 mm for passing light, and the gap is 1 to 8 mm wide.

8. The turbidity sensor according to claim 6, further comprising a positive lens placed inside one of the cavities and between said light stop and said first cylinder.

9. The turbidity sensor according to claim 8, wherein the positive lens is a ball lens having diameter of 2 to 4 mm.

10. A turbidity sensor for underwater measurements, comprising:
    a watertight housing;
    a light emitting diode;
    a first light focusing device for focusing a light emitted from the diode and passing the focused light into to-be-measured water;

a second light focusing device for collecting at least one scattered light resulted form the focused light when passing the water;

a photodiode for receiving the collected light thereby generating electronic signals; and an electronic board for processing the electronic signals, wherein said watertight housing has cavities for accommodating the first and second focusing devices therein respectively, said cavities are shaped cylindrically and tilted with a first angle relatively to an upper surface of said watertight housing which is placed below a water surface, and the first and second focusing devices are ball lenses placed inside of said tilted cylindrical cavities.

11. The turbidity sensor according to claim 10, further comprising two optical windows located in the watertight housing and in parallel with the upper surface of the watertight housing, wherein the windows are optically communicating with the ball lenses, and at least one space between the ball lens and the windows is filled with a transparent material.

12. The turbidity sensor according to claim 11, wherein said transparent material comprises a transparent potting compound.

13. The turbidity sensor according to claim 11, wherein said transparent material comprises an optical glue.

14. The turbidity sensor according to claim 6, further comprising a first optical fiber optically connecting the light stop and the light emitting diode, and a second optical fiber optically connecting the second cylinder and the photodiode.

15. A turbidity sensor for underwater measurements, comprising:
a watertight housing;
a light emitting diode;
a first light focusing device for focusing a light emitted from the diode and passing the focused light into to-be-measured water;
a second light focusing device for collecting at least one scattered light resulted form the focused light when passing the water;
a photodiode for receiving the collected light thereby generating electronic signals; and
an electronic board for Processing the electronic signals, wherein said watertight housing has cavities for accommodating the first and second focusing devices therein respectively, said cavities are shaped cylindrically and tilted with a first angle relatively to an upper surface of said watertight housing which is placed below a water surface, said cavities further include a semi-spherical shared end connecting with the upper surface of the housing, and the first and second focusing devices are transparent half ball lenses having a spherical surface from one side and a flat surface from other side therein said half ball lenses fitting in said cavities and having the flat surfaces parallel to the flat surface of the watertight housing.

16. The turbidity sensor according to claim 15, wherein the light emitting diode and the photodiode are placed under one of said half ball lenses along the cylindrical cavities respectively.

17. The turbidity sensor according to claim 16, further comprising a light stop placed inside one of the cavities and between the light emitting diode and said semi-spherical surface of a first ball lens of said ball lens such that a gap is provided between the light stop and said semi-spherical surface of the first ball lens.

18. The turbidity sensor according to claim 17, wherein said light stop has an opening with a diameter of 0.3 to 3 mm for passing light, and the gap is 1 to 8 mm wide.

19. The turbidity sensor according to claim 15, further comprising two optical windows located in the watertight housing and in parallel with the upper surface of the watertight housing, and the windows are optically communicating with the flat ends of said half ball lens respectively.

20. The turbidity sensor according to claim 19, wherein said optical windows made of sapphire.

21. The turbidity sensor according to claim 16, wherein said half ball lenses are made of glass and having a diameter of 3 to 7 mm, and wherein the first angle ranges from 49° to 53°

22. The turbidity sensor according to claim 17, wherein said half ball lenses are made of sapphire and having a diameter of 4 to 8 mm, and wherein the first angle ranges from 56° to 60°.

23. The turbidity sensor according to claim 15, further comprising a first ball lens placed between the photodiode and the semi-spherical surface of a second hail ball lens of said half ball lens.

24. The turbidity sensor according to claim 23, further comprising a first optical fiber optically connecting the light stop and the light emitting diode, and a second optical fiber optically connecting the first ball lens and the photodiode.

25. The turbidity sensor according to claim 24, further comprising a second ball lens placed between the fist fiber and the light emitting diode, and a third ball lens placed between the second fiber and the photodiode.

26. A turbidity sensor for underwater measurements, comprising:
a watertight housing;
a light emitting diode;
a first light focusing device for focusing a light emitted from the diode and passing the focused light into to-be-measured water;
a second light focusing device for collecting at least one scattered light resulted form the focused light when passing the water;
a photodiode for receiving the collected light thereby generating electronic signals; and
an electronic board for processing the electronic signals, wherein said watertight housing has cavities for accommodating the first and second focusing devices therein respectively, said cavities are shaped cylindrically and tilted with a first angle relatively to an upper surface of said watertight housing which is placed below a water surface, and further comprising an optical calibrator accommodated by a third cavity inside of said watertight housing.

27. The turbidity sensor according to claim 26, wherein the optical calibrator has an electrical switch for enabling or disabling the optical calibrator.

28. The turbidity sensor according to claim 26, wherein the third cavity include a first cylindrical channel for accommodating the optical calibrator therein, and the third cavity is positioned perpendicular to the upper surface of the housing such that a light reflecting means or a shutter of the optical calibrator is moved along the first cylindrical channel by a moving means to enable or disable the optical calibrator.

29. The turbidity sensor according to claim 28, wherein the electrical switch drives the light reflecting means or the shutter to move along the first cylindrical channel.

30. The turbidity sensor according to claim 29, wherein the electrical switch comprises an electromagnet.

31. The turbidity sensor according to claim 28, wherein the shutter is opaque, and the optical calibrator further includes two pieces of optic fiber separated by the opaque shutter.

32. The turbidity sensor according to claim 28, wherein the light reflecting means comprises a mirror, and the optical calibrator further comprises a movable mirror holder with one position allowing the mirror reflects at least a portion of the light from the first light focusing device into the second light focusing device and another position for blocking said portion of the light.

33. The turbidity sensor according to claim 32, wherein the third cavity further comprising a second and a third cylindrical channels for passing said portion of the light, and a light reflected by the mirror.

34. The turbidity sensor according to claim 32, wherein the movable holder moves outside of the watertight housing to move the mirror above the upper surface of the housing so as to reflect said portion of the light.

35. A turbidity sensor for underwater measurements, comprising:
- a watertight housing;
- a light emitting diode;
- a first light focusing device for focusing a light emitted from the diode and passing the focused light into to-be-measured water;
- a second light focusing device for collecting at least one scattered light resulted form the focused light when passing the water;
- a photodiode for receiving the collected light thereby generating electronic signals; and
- an electronic board for processing the electronic signals, wherein said watertight housing has cavities for accommodating the first and second focusing devices therein respectively, said cavities are shaped cylindrically and tilted with a first angle relatively to an upper surface of said watertight housing which is placed below a water surface, and further comprising an optical calibrator placed outside of said watertight housing and comprises a transparent member movable above the said optical windows having one side transparent and another side comprising reflective or diffusing surface able to direct part of the excitation beam into a third focusing device.

36. The turbidity sensor according to claim 35, wherein the electrical drive comprises an electrical motor operable to rotate the optical calibrator from the position when it is illuminated by light beam into position when light beam is not restricted and turbidity of water should be measured.

37. The turbidity sensor according to claim 35, wherein a soft cleaning member fixed stationary near or around the said windows therein a transparent surface of the optical calibrator can be cleaned from the possible contamination.

38. The turbidity sensor according to claim 35, further comprising a first optical filter placed between the second ball lens and the light emitting diode, and a second optical filter placed between the third ball lens and the photodiode.

39. The turbidity sensor according to claim 38, therein said optical filters are arranged to be movable and made of at least two parts with different spectral transmission.

\* \* \* \* \*